United States Patent [19]

Araki et al.

[11] 4,398,051

[45] Aug. 9, 1983

[54] PRODUCTION OF TERTIARY OLEFINS

[75] Inventors: Masashi Araki; Takuo Hibi, both of Ichihara; Tomofumi Kawabe; Takeshi Yamahara, both of Chiba, all of Japan

[73] Assignee: Sumitomo Chemical Company, Limited, Osaka, Japan

[21] Appl. No.: 312,344

[22] Filed: Oct. 16, 1981

[30] Foreign Application Priority Data

Oct. 28, 1980 [JP] Japan ................................. 55-151661
Feb. 27, 1981 [JP] Japan ................................. 56-29147

[51] Int. Cl.$^3$ ............................................. C07C 1/00
[52] U.S. Cl. ..................................... 585/640; 585/639
[58] Field of Search ........................................ 585/640

[56] References Cited

U.S. PATENT DOCUMENTS

| | | | |
|---|---|---|---|
| 3,170,000 | 2/1965 | Verdol | 585/640 X |
| 3,401,210 | 9/1968 | de Jongh | 585/639 X |
| 4,006,198 | 2/1977 | Tesei et al. | 585/640 |
| 4,147,763 | 4/1979 | Gokhberg et al. | 585/640 X |
| 4,254,296 | 3/1981 | Manara et al. | 585/640 |
| 4,320,232 | 3/1982 | Volkamer et al. | 585/639 X |

*Primary Examiner*—Paul F. Shaver
*Attorney, Agent, or Firm*—Wenderoth, Lind & Ponack

[57] ABSTRACT

Method of producing tertiary olefins from alkyl tert-alkyl ethers using a catalyst produced by calcining an aluminum compound supported on a carrier containing silicon oxides at a temperature above that at which the aluminum compound decomposes.

12 Claims, No Drawings

PRODUCTION OF TERTIARY OLEFINS

The present invention relates to a method for the production of tertiary olefins. More particularly, it relates to a method for the production of tertiary olefins from alkyl tert-alkyl ethers.

Tertiary olefins have so far been commercially produced by the sulfuric acid extraction method. Since this method uses sulfuric acid of high concentrations, the use of expensive materials for the apparatus is essential. Besides, this method is not always advantageous industrially, because tertiary olefins cause side reactions such as polymerization, hydration and the like during extraction with concentrated sulfuric acid.

It is well known that tertiary olefins easily react with a primary alcohol in the presence of an acid catalyst to produce the corresponding alkyl tert-alkyl ethers. It is also well known that, when tertiary olefins form mixtures with other olefinic hydrocarbons, they alone likewise react selectively with a primary alcohol.

For producing tertiary olefins from alkyl tert-alkyl ethers thus obtained, there have so far been proposed some methods using the following catalysts: For example, γ-alumina catalysts (Japanese Patent Publication No. 41882/1972), alumina catalysts modified with a silicon compound (Japanese Patent Kokai No. 39604/1976), metal sulfate catalysts (Japanese Patent Publication No. 26401/1976), and silica catalysts modified with a metallic ion (Japanese Patent Kokai No. 2695/1980).

All these methods are however unsatisfactory for the following reasons: Recovery of the alcohol is poor because of formation of an ether as by-product; the reaction temperature is high; preparation of the catalyst is very troublesome; and expensive reagents are necessary.

We have found that high-purity tertiary olefins are obtainable in high yields by bringing alkyl tert-alkyl ethers into contact with a specified catalyst.

Thus, in the method of producing tertiary olefins using alkyl tert-alkyl ethers as raw material, the present invention provides a method characterized by using a catalyst produced by supporting an aluminum compond on a carrier containing silicon oxides, followed by calcining at a temperature above the temperature at which said aluminum compound decomposes.

According to the present invention, production of the catalyst is very simple, and high-purity tertiary olefins are obtained in high yields in the presence of said catalyst.

The starting material to be used in the present invention is an alkyl tert-alkyl ether. The ethers are generally obtained by the reaction of the foregoing tertiary olefins with primary alcohols but without being limited to this method. Examples of the ethers include methyl tert-butyl ether, ethyl tert-butyl ether and methyl tert-amyl ether.

The catalyst to be used in the present invention may be produced by the calcination of an aluminum compound supported on a carrier containing silicon oxides at a temperature above that at which said aluminum compound decomposes.

In the present invention, as a method for supporting the aluminum compound on the carrier, impregnation of the carrier containing silicon oxides with the aluminum compound (e.g. equilibrium adsorption method, evaporation-to-dryness method, spraying method) is preferred. However, other methods, for example methods wherein the carrier powder and the aluminum compound are uniformly mixed in the dry state or uniformly kneaded in the slurry state and then molded, may be employed. In short, the catalyst of the present invention is obtained by calcining the aluminum compound and the carrier containing silicon oxides together, thereby decomposing the aluminum compound.

The aluminum compound is not particularly limited, but generally, aluminum compounds which decompose at less than 1500° C. are selected taking into account the calcination temperature and the thermal resistance of the carrier. Specifically, the aluminum compound includes, for example, the sulfate, nitrate, halides, organic acid salts and hydroxide of aluminum. Of these, the sulfate and nitrate are particularly preferred.

Generally, the calcination temperature is selected within a range from a temperature at which the aluminum compound decomposes to 1500° C. The temperature at which the aluminum compound decomposes, as referred to herein, does not mean the so-called decomposition temperature described in the literature, but rather a temperature at which the aluminum compound in the carrier-supported state begins to decompose practically. This temperature is generally lower than the decomposition temperature, although it depends upon the purity of the aluminum compound. Decomposition of the aluminum compound, for example aluminum sulfate and aluminum nitrate, can easily be confirmed by the evolution of sulfur oxides and nitrogen oxides, respectively. Specifically, the calcining temperature is preferably 500° to 1200° C., more preferably 700° to 1000° C., although it depends upon the kind of aluminum compound. In case the aluminum compound is aluminum sulfate or aluminum nitrate, a preferable calcining temperature is within the range of 700° to 1200° C., more specifically from 750° to 1000° C.

The calcination is generally carried out in the air, but an atmosphere of an inert gas (e.g. nitrogen, carbon dioxide, argon), steam or mixtures thereof may also be used.

The time for calcination is generally 0.1 to 24 hours, preferably 0.5 to 10 hours, although it depends upon the calcination temperature. The amount of the aluminum compound supported on the carrier is 0.1 to 100 parts by weight, preferably 1 to 50 parts by weight, more preferably 5 to 30 parts by weight, based on 100 parts by weight of the carrier (when the aluminum compound contains water of crystallization, the amount needs to be converted to an anhydride basis).

As examples of the carrier containing silicon oxides used in the present invention, there may be mentioned minerals such as silica, montmorillonite, kaolinite, attapulgite, bentonite and acid clay. Besides there, silica-alumina, silica-zirconia, silica-magnesia and their mixtures may also be used. Silica may be used in either the form of gel or sol. A particularly preferred carrier is one prepared from silica or montmorillonite type minerals. The surface area of the carrier is not particularly limited, but preferably, it is more than 1 m$^2$/g.

The performance of the catalyst used in the present invention is superior in activity and selectivity to any of the carriers containing silicon oxides or simple thermal-decomposed aluminum compounds or their mixtures. This means, although details are not clear, that the presence of silicon oxides is essential to the thermal decomposition of the aluminum compound. Besides, the catalyst of this invention promises an extended catalytic life which is most required in industrial use.

In carrying out the method of the present invention, a gas-phase reaction on fixed-bed form is generally employed, but other forms such as a fluidized-bed may also be used. The reaction temperature is generally 100° to 400° C., preferably 150° to 300° C. The reaction pressure is not particularly limited, but generally, it is atmospheric pressure to 20 kg/cm², preferably atmospheric pressure to 10 kg/cm². The feed rate of material varies with the reaction temperature, reaction pressure, required conversion of alkyl tert-alkyl ethers, etc., but generally, it is 1 to 50, preferably 3 to 20, as expressed in LHSV. Further, the ethers as material may be used for the reaction in admixture with an inert gas or steam.

The present invention will be illustrated in more detail with reference to the following examples, which are not however to be interpreted as limiting the scope of the invention.

EXAMPLE 1

A commercially available silica carrier (Silica N-608, trade name, produced by Nikki Kagaku K.K.) was pulverized to 10 to 24-mesh in size. Ten parts (converted to an anhydride basis) of aluminum sulfate was supported on 100 parts of the carrier by the impregnation method. The supported aluminum sulfate was dried in air at 130° C. for 3 hours and at 350° C. for 3 hours, and then calcined at 900° C. for 5 hours in nitrogen atmosphere. During the calcining, evolution of sulfur oxides was observed.

Ten milliliters of this catalyst was packed in a quartz reactor, and methyl tert-butyl ether was supplied to the reactor at a rate of 49 ml/hr (LHSV=4.9 hr⁻¹) under atmospheric pressure, during which the temperature of the center of the catalyst layer was maintained at 180° C. by means of an electric furnace. Analysis of the trapped reaction gas showed that the conversion of methyl tert-butyl ether was 99.4%. Isobutylene was obtained quantitatively and the formation of dimethyl ether was not observed.

EXAMPLES 2 TO 9

Catalysts were prepared in the same manner as in Example 1, and decomposition of methyl tert-butyl ether was carried out using the catalysts. In any case, isobutylene was obtained in quantitative amounts corresponding to the conversion of the ether. The results are shown in Table 1.

TABLE 1

| | Catalyst preparation | | | | Reaction results | | | |
|---|---|---|---|---|---|---|---|---|
| Example | Aluminum compound | Amount supported (1) | Silica (2) | Calcination condition | Temperature of the center of the catalyst layer (°C.) | LHSV (hr⁻¹) | Conversion of MTBE (%) (3) | Selectivity of dimethyl ether (%) (4) |
| 2 | Aluminum sulfate | 10 | N-608 | 600° C. 5 hr | 161 | 9.6 | 83 | 0.00 |
| 3 | Aluminum sulfate | 1 | N-601 | 900° C. 5 hr | 245 | 4.9 | 86.3 | 0.13 |
| 4 | Aluminum sulfate | 3 | " | " | 210 | 4.9 | 96.8 | 0.15 |
| 5 | Aluminum sulfate | 5 | " | " | 203 | 4.9 | 99.4 | 0.17 |
| 6 | Aluminum sulfate | 1 | N-608 | " | 270 | 5.3 | 96.9 | 0.05 |
| 7 | Aluminum sulfate | 10 | N-601 | " | 153 | 4.7 | 99.4 | 0.10 |
| 8 | Aluminum sulfate | 30 | " | " | 137 | 5.0 | 85.8 | 0.03 |
| 9 | Aluminum nitrate | 10 | N-608 | " | 247 | 5.1 | 99.8 | 0.14 |

Note:
(1): Amount (part by weight converted to an anhydride basis) of the aluminum compound based on 100 parts of silica.
(2): Trade names of silica produced by Nikki Kagaku K.K.
(3): MTBE . . . methyl tert-butyl ether
(4): Calculated from the following equation:

$$\left( \frac{\text{Moles of produced dimethyl ether}}{\text{Moles of reacted MTBE}} \right) \times 2 \times 100 \, (\%)$$

EXAMPLE 10

Reaction was carried out in the same manner as in Example 1 except that a SUS reactor was used, the temperature of the center of the catalyst layer was 190° C., the reaction pressure was 6 kg/cm² (gauge pressure), and the LHSV was 5.3 hr⁻¹. As a result, the conversion of methyl tert-butyl ether was 96.9%, the selectivity of dimethyl ether was 0.3% and isobutylene was obtained quantitatively.

EXAMPLE 11

Reaction was carried out in the same manner as in Example 1 except that ethyl tert-butyl ether was used as a material. As a result, the conversion of the ether was 98.8% and isobutylene was obtained quantitatively and the formation of diethyl ether was not observed.

EXAMPLE 12

19.2 parts (converted to an anhydride basis) of aluminum sulfate was supported on 100 parts of a montmorillonite type carrier (KA-1, trade name, produced by Nissan Girdler Catalyst Co.) by the impregnation method. The supported aluminum sulfate was dried at 350° C. for 3 hours and calcined at 900° C. for 5 hours. During the calcination, evolution of sulfur oxides was observed. The catalyst thus obtained was pulverized to 10 to 24-mesh in size and packed in a quartz reactor equipped with a vaporizer. Thereafter, decomposition of methyl tert-butyl ether was carried out under atmospheric pressure while heating the reactor to 190° C. in an electric furnace.

The ether was supplied to the reactor at an LHSV of 5 hr$^{-1}$, and as a result, the temperature of the center of the catalyst layer was 120° C. Analysis of the gas from the reactor outlet showed that the conversion of methyl tert-butyl ether was 92.4%, and that the selectivity of dimethyl ether was 0.03% based on the reacted methyl tert-butyl ether. Isobutylene was thus obtained quantitatively.

COMPARATIVE EXAMPLE 1

Reaction was carried out in the same manner as in Example 12 except that a carrier with no aluminum sulfate supported thereon was used, and the reactor was heated to 209° C. from the outside. As a result, the temperature of the center of the catalyst layer was 165° C., and the conversion of methyl tert-butyl ether was 69.2%. On comparing with the results of Example 12, the activity of the catalyst was lower although the reaction temperature was higher, from which the effect of the present invention is clearly shown.

EXAMPLES 13 TO 16

Reaction was carried out in the same manner as in Example 12 but using the reaction conditions shown in Table 2. The results are also shown in Table 2.

TABLE 2

| Example | Amount of aluminum sulfate supported on 100 parts of the carrier | Calcination condition | Outside temperature of the reactor (°C.) | Conversion of MTBE (%) (1) | Selectivity of DME (%) (2) |
|---|---|---|---|---|---|
| 13 | 18.9 | 600° C. 5 hr | 190 | 79.4 | 0.01 |
| 14 | 7.3 | 900° C. 5 hr | 190 | 88.1 | 0.02 |
| 15 | 12.2 | 900° C. 5 hr | 190 | 91.6 | 0.02 |
| 16 | 30.6 | 900° C. 5 hr | 190 | 92.3 | 0.02 |

Note:
(1): Methyl tert-butyl ether
(2): Dimethyl ether

EXAMPLE 17

Reaction was carried out in the same manner as in Example 12 except that the catalyst was prepared by supporting 20 parts of aluminum sulfate on 100 parts of silica alumina [N-631(L), trade name of Nikki Kagaku K.K., pulverized to 10 to 24-mesh in size] according to the evaporation-to-dryness method, followed by drying at 350° C., for 3 hours and calcining at 900° C. for 5 hours. When the outside temperature of the reactor and LHSV were maintained at 189° C. and 5.2 hr$^{-1}$, respectively, the temperature of the center of the catalyst layer was 111° C. As a result, the conversion of methyl tert-butyl ether was 97.2%, and the selectivity of dimethyl ether was 0.2%.

COMPARATIVE EXAMPLE 2

Reaction was carried out in the same manner as in Example 17 except that the catalyst was prepared by calcining silica-alumina [N-631(L), trade name of Nikki Kagaku K.K., pulverized to 10 to 24-mesh in size] at 900° C. for 5 hours. When the outside temperature of the reactor and LHSV were maintained at 190° C. and 5.2 hr$^{-1}$, respectively, the temperature of the center of the catalyst layer was 106° C. As a result, the conversion of methyl tert-butyl ether was 89.6% and the selectivity of dimethyl ether was 0.1%.

EXAMPLE 18

The experiment of Example 12 was carried out as follows in a pressurized system: Methyl tert-butyl ether containing 1.6 wt.% of water was used as a starting material; a SUS reactor was used; the pressure of the reaction system was kept at 6 kg/cm$^2$ (gauge pressure); the outside temperature of the reactor was kept at 208° C.; and LHSV was 5.3 hr$^{-1}$. Under this condition, the temperature of the center of the catalyst layer was 170° C. As a result, the conversion was 95.9% and the selectivity of dimethyl ether was 0.16%.

EXAMPLE 19

Eighteen parts of aluminum sulfate were supported on 100 parts of a commercially available silica carrier (Silica N-601, trade name, produced by Nikki Kagaku K.K.). The supported aluminum sulfate was calcined at 800° C. for 3 hours to obtain a catalyst. By the use of this catalyst methyl tert-butyl ether containing 1.5% of water was decomposed. The decomposition was conducted continuously at a rate of LHSV 5.2 hr$^{-1}$ and 7 kg/cm$^2$ (gauge) while externally heating by means of an electric furnace. After the initial deactivation there was obtained a constant catalytic activity. The temperature at the center of the catalyst layer was 230° C. The conversion of methyl tert-butyl ether was 97%, and selectivity of dimethyl ether was 0.5%. After continuous operation for 2100 hours the conversion was 96% and the selectivity of dimethyl ether was 0.5%, so that there was no substantial deactivation of the catalyst.

COMPARATIVE EXAMPLE 3

Aluminum sulfate without being supported on a carrier was dried at 350° C. for 3 hours and then calcined at 900° C. for 5 hours. By the use of this catalyst the decomposition reaction of methyl tert-butyl ether was conducted in the same manner as in Example 1. At LHSV 4.8 hr$^{-1}$ and a temperature of 239° C. at the center of the catalyst, the conversion was 99.9% and the selectivity of dimethyl ether was 50.7%. When the temperature of the center of the catalyst was lowered to 207° C. while maintaining the same LHSV, the conversion was 74.7% and the selectivity of dimethyl ether was 13.7%. Upon X-ray diffraction analysis it was observed that the catalyst in this case was in the form of gamma aluminum, which apparently was not favorable because of the formation of a large amount of dimethyl ether as compared with the catalyst of the present invention.

What we claim is:

1. In a method of producing a tertiary olefin using an alkyl tert-alkyl ether as raw material, the improvement wherein the method is conducted in the presence of a catalyst produced by supporting at least on part by weight of an aluminum compound on 100 parts by weight of a carrier containing silicon oxides and calcining the resultant produce at a temperature above the temperature at which said aluminum compound decomposes.

2. A method according to claim 1, wherein said aluminum compound is aluminum sulfate, aluminum nitrate or aluminum hydroxide.

3. A method according to claim 2, wherein the aluminum compound is aluminum sulfate or aluminum nitrate.

4. A method according to claim 1, wherein said carrier containing silicon oxides is one prepared from silica or montmorillonite type minerals.

5. A method according to claim 1, wherein the amount of the aluminum compound supported on the carrier is 1 to 50 parts by weight based on 100 parts by weight of the carrier.

6. A method according to claim 1, wherein the amount of aluminum sulfate or aluminum nitrate supported on the carrier is 5 to 30 parts by weight based on 100 parts by weight of the carrier.

7. A method according to claim 1, wherein the calcining temperature is 500° to 1200° C.

8. A method according to claim 1, wherein the calcining temperature is 700° to 1000° C.

9. A method according to claim 1, wherein the calcining temperature is 700° to 1200° C.

10. A method according to claim 1, wherein the calcining temperature nitrate supported on the carrier is 750° to 1000° C.

11. A method according to claim 1, wherein said alkyl tert-alkyl ether is methyl tert-butyl ether.

12. A method according to claim 1, wherein the aluminum compound is supported on a carrier by an impregnation method.

* * * * *